United States Patent [19]
Ugai et al.

[11] Patent Number: 5,756,899
[45] Date of Patent: May 26, 1998

[54] INTEGRATED SENSOR

[75] Inventors: Seiichi Ugai; Yasunori Shoji; Yasushi Shimizu, all of Hitachinaka, Japan

[73] Assignee: Hitachi, Ltd., Tokyo, Japan

[21] Appl. No.: 846,936

[22] Filed: Apr. 30, 1997

[30] Foreign Application Priority Data

May 1, 1996 [JP] Japan ................... 8-110731

[51] Int. Cl.[6] .................................................. G01L 7/00
[52] U.S. Cl. ................... 73/714; 73/716; 73/718; 73/719; 73/725
[58] Field of Search ................... 73/714, 716, 717, 73/718, 719, 720, 721, 723, 724, 725, 726, 727, 700, 335.04, 335.05

[56] References Cited

U.S. PATENT DOCUMENTS

| | | | |
|---|---|---|---|
| 3,787,764 | 1/1974 | Andeen et al. | 73/718 X |
| 4,339,719 | 7/1982 | Rhines et al. | |
| 4,445,383 | 5/1984 | Binder et al. | 73/718 |
| 4,625,560 | 12/1986 | Sanders | 73/718 |
| 4,730,496 | 3/1988 | Knecht et al. | 73/724 |
| 4,831,492 | 5/1989 | Kuisma | 73/724 X |
| 5,142,912 | 9/1992 | Frische | 73/727 X |
| 5,157,973 | 10/1992 | Ciminelli | 73/718 |
| 5,353,628 | 10/1994 | Bellows | 73/25.01 |
| 5,469,749 | 11/1995 | Shimada et al. | 73/721 X |
| 5,515,732 | 5/1996 | Willcox et al. | 73/724 |
| 5,629,538 | 5/1997 | Lipphardt et al. | 73/720 X |

Primary Examiner—Geroge M. Dombroske
Assistant Examiner—Paul Amrozowicz
Attorney, Agent, or Firm—Kenyon & Kenyon

[57] ABSTRACT

The first glass substrate having the first pressure admitting entrance for leading the pressure of fluid to be measured, is arranged at a side of a diaphragm of a pressure sensor, for measuring differential pressure. The second glass substrate is arranged at the side opposite to the first glass substrate, a spacer being sandwiched therebetween. The second pressure admitting entrance is formed at the second glass substrate, at the position opposite to the first presser admitting entrance of the first glass substrate. The first conductive film and the second conductive film are formed on two surfaces facing to each other, of the first and second glass substrates, respectively. By measuring the specific conductance and the dielectric constant of the object fluid between the two conductive films, these physical constants indicating the quality of the fluid, the quality of the fluid can be also detected. Thus, it becomes possible to realize and provide an integrated sensor capable of measuring the differential pressure (flow rate) and the quality of fluid by using one transmitter.

21 Claims, 15 Drawing Sheets

TOP SURFACE

BOTTOM SURFACE

TOP SURFACE

BOTTOM SURFACE

TOP SURFACE

BOTTOM SURFACE

INTEGRATED SENSOR

BACKGROUND OF THE INVENTION

1. Field of the Invention

The present invention relates to an integrated sensor used for measuring a water level, a temperature, a flow rate, the quality of water and so forth in an agriculture reservoir and a water filter plant, and used in the instrumentation in the industry.

2. Description of Related Art

As an example of an integrated sensor, a piezo-resistive integrated sensor used at a sensing part of an intelligent differential pressure transmitter is existing. This piezo-resistive integrated sensor is composed of a differential pressure sensor, a static presser sensor and a temperature sensor formed on a substrate, wherein a differential presser is measured with high accuracy by correcting an output of the differential pressure sensor with output signals of the static pressure sensor and the temperature sensor.

Now, strengthening of water acidifying in a reservoir due to the acid rain or a geological feature surrounding the reservoir, and the deterioration of water quality becomes a important problem. Further, it is necessary to precisely detect a water level and control the level so as to keep constant, of a reservoir, because the flowing amount of reversely flowing into the reservoir changes, depending on seasons.

In working for a rice crop, since farmers open and close a number of feed-water pumps and draining pumps, much labor and cost is necessary to keep the adequate levels of rice paddies, corresponding to a much rain season or a little rain season. Therefore, it is difficult to keep the rice paddies of a large area adequate situations by a few farmers.

Further, since it is rare to control the quality of water and measure the quantity of fertilizer dissolving in the water, it has been a problem in that growth of rice receives bad influences of a delay of giving the water and additional fertilizer or an addition of excessive fertilizer.

In rice paddies of a large area, it is needed that the amount of feed water is accurately detected and controlled, since water is fed to the rice paddies by using pipe lines.

Therefore, the water level, the flow rate, or the quality of water and forth should be correctly detected in each reservoir or each rice paddy.

Although using the above-mentioned intelligent differential transmitter may be considered for detecting the water level, the flow rate, or the quality of water and forth, an existing intelligent differential transmitter can measure only one of the water level, the flow rate and the quality of water, for example, only the flow rate of fed water or drained water. Therefore, in order to simultaneously measure the water level, the flow rate and the quality of water, a plurality of respective transmitters of a water level sensor, a pressure sensor and a water quality sensor are to be used, of which operations and maintenance become very complicated.

Thus, it has been desired to realize an integrated sensor capable of measuring a water level, a flow rate, a water quality, and so forth, by using one transmitter.

SUMMARY OF THE INVENTION

An objective of the Invention

An objective of the present invention is to provide an integrated sensor capable of measuring a water level, a flow rate and a water quality by using one transmitter, of a reservoir or a rice paddy.

Method solving the Problem (1) To attain the above-mentioned objective, the present invention provides an integrated sensor, comprising:

a pressure sensor including a diaphragm displacing corresponding to a pressure of an object substance to be measured;

a first substrate connected to the diaphragm, possessing a first pressure admitting entrance for admitting the pressure of the substance to be measured, to the diaphragm, and a first conductive film formed on a surface of the first substrate;

a second substrate possessing a second pressure admitting entrance for admitting the pressure of the substance to be measured, to the diaphragm, via the first pressure admitting entrance, and a second conductive film at the position of a surface of the second substrate, facing to the first conductive film, the two conductive films being separated by the predetermined interval; and a signal processing unit for measuring the specific conductance and the dielectric constant of the substance filled between the first conductive film and the second conductive film, and the pressure of the substance, by using output signals transmitted from the pressure sensor.

Since this integrated sensor can detect the specific conductance and the dielectric constant as a feature parameter of a water quality, it is possible to realize or provide an integrated sensor capable of measuring a water level, a flow rate and a water quality by using one sensor.

(2) In the sensor described in (1), the diaphragm in the pressure sensor is preferably made of single crystal silicon, at which a temperature sensitive element is provided, and the signal processing unit measures the temperature of the substance in the vicinity of the pressure sensor by using an output signal transmitted from the temperature sensitive element.

(3) In the sensor described in (1), preferably, a strain-sensitive gauge element is provided on a surface of the diaphragm in the pressure sensor, another surface of the diaphragm is connected to the first substrate.

(4) In the sensor described in (1), preferably, a strain-sensitive gauge element is provided on a surface of the diaphragm in the pressure sensor, the surface of the diaphragm, on which the strain-sensitive gauge element, is connected to the first substrate.

(5) In the sensor described in (1), preferably, a first electrode plate is provides at a position of the first substrate, facing to the diaphragm which is a conductive electrode, and a second electrode plate is provided at a position opposite to the first electrode plate so that the two electrode plates sandwich the diagram, and the signal processing unit measures the pressure generated by the substance, based on a difference between, an electrostatic capacity between the first electrode plate and the diaphragm and an electrostatic capacity between the second electrode plate and the diaphragm.

(6) In the sensor described in (1), preferably, the pressure sensor is made of single crystal silicon, the first substrate is made of boro-silicated glass, and the pressure sensor is airtightly connected to the first substrate by a anodic bonding method.

(7) In the sensor described in (1), preferably, the pressure sensor is made of single crystal silicon, and one of an oxidation film, a nitriding film and a corrosion-resistant metal film is formed at a surface area exposed to the substance, in the pressure sensor.

(8) In the sensor described in (1), preferably, the first conductive film and the second conductive film are made of corrosion-resistant metal film.

(9) In the sensor described in (1), preferably, for at least one of the first substrate and the second substrate, a through-hole is provided for electrically connecting the conductive film on a surface of the substrate and the conductive film on another surface of the substrate.

(10) In the sensor described in (1), preferably, the first conductive film and the second conductive film are connected to terminals provided at the signal processing unit via electrical connection wires, and a covering member for protecting the first conductive film, the second conductive film and the electrical connection wires from the substance, is attached to at least the second substrate.

(11) In the sensor described in (1), preferably, the pressure of the substance is led to a surface of the diaphragm via the first pressure admitting entrance and the second pressure admitting entrance, and another surface of the diaphragm is contained in an isolation chamber.

(12) In the sensor described in (11), preferably, the pressure of the isolation chamber is kept constant.

(13) In the sensor described in (11), preferably, the isolation chamber is kept at an almost vacuum state.

(14) In the sensor described in (11), preferably, at least one pressure admitting passage line leading to the isolation chamber is provided to set the pressure of the isolation chamber as a desired level.

(15) In the sensor described in (11), preferably, the substance to be measured is liquid, the pressure of the liquid is led to the a surface of the diaphragm, and a pressure admitting passage line leading to the isolation chamber is provided to set the pressure of the isolation chamber as the atmosphere pressure.

(16) In the sensor described in (11), preferably, the substance is fluid flowing in a pipe in which an orifice is provided, the pressure of the fluid in the upstream from the orifice is led to a surface of the diaphragm via the first pressure admitting entrance and the second pressure admitting entrance, and a pressure leading path is provided in the isolation chamber, in order to lead the pressure of the fluid in the downstream from the orifice to another surface of the diaphragm.

(17) In the sensor described in (15), preferably, at least a part of the signal processing unit is placed over the surface of liquid, which is separated from and electrically connected to the pressure sensor with a waterproofing wire.

(18) In the sensor described in (15), preferably, at least a part of the signal processing unit is placed over the surface of liquid, which is separated from and electrically connected to the pressure sensor, a pressure leading path is connected between the signal processing unit and the isolation chamber, and a signal transmitting wire for connecting the signal processing unit and the pressure sensor is arranged in the presser leading path.

(19) A fluid management system including a fluid storing part, a fluid feeding part with a first control valve for flowing fluid into the fluid storing part, a fluid draining part with a second control valve for draining fluid from the fluid storing part, a control part for adjusting the level of fluid in the fluid storing part by controlling the first control valve at the fluid feeding part and the second control valve at the fluid draining part, wherein the above-mentioned integrated sensor is arranged in the fluid storing part, and the control part adjusts the level of fluid in the fluid storing part by controlling the first control valve, detects the specific conductance expressing a liquid quality and generates an alarm if the detected specific conductance is out of the predetermined range, based on output signals transmitted from the integrated sensor.

(20) A method of producing an integrating sensor, comprises the steps of:

forming a through-hole uses for a first pressure admitting entrance at a first insulating substrate;

forming a first conductive film on at least one surface of the first substrate;

forming a through-hole uses for a second pressure admitting entrance at a second insulating substrate, and forming a second conductive film on at least one surface of the second substrate;

connecting a pressure sensor to another surface of the first substrate so that a diaphragm in the pressure sensor is opposite to the first pressure admitting entrance;

combining the first substrate and the second substrate by inserting an insulating spacer between both substrates so that the first conductive film formed on the first substrate faces to the second conductive film formed on the second substrate, and the first pressure admitting entrance also faces to the second pressure admitting entrance;

connecting a sealing member including a concave part and a connection terminal, to the first substrate, so that the concave part contains the pressure sensor; and connecting the first conductive film, the second conductive film and the pressure sensor to the connection terminal, by wiring among them.

DETAILED DESCRIPTION OF THE EMBODIMENTS

Figure 1:
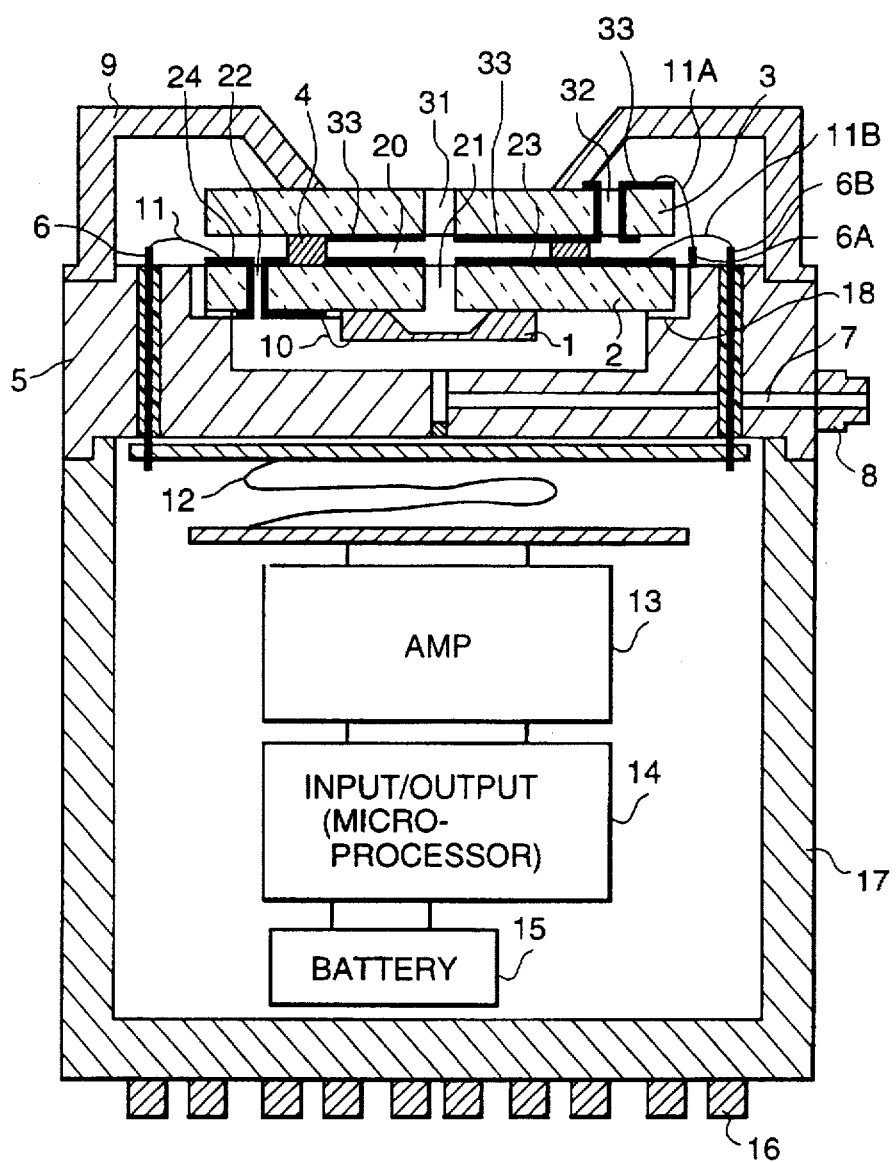
FIG. 1 is an outline sectional view of an integrated sensor of a first embodiment according to the present invention.

Hereinafter, details of the present invention will be explained with reference to embodiments shown in the drawings.

FIG. 1 is an outline sectional view of an integrated sensor of a first embodiment according to the present invention.

In FIG. 1, a pressure sensor 1 possesses a diaphragm of a piezo-gauge, an evaporation deposition gauge, etc., made of single crystal silicon, which is displaced by an applied pressure, and gauge resistors are formed on the diaphragm. The pressure sensor 1 is connected to the first glass substrate 2 (a lower substrate) made of, for example, boro-silicated glass so that the gauge resistor faces to a first glass substrate.

Further, another surface contrary to the surface of the first glass substrate 2, on which the pressure sensor is attached, is connected to a second glass substrate 3 (an upper substrate), the two substrates sandwiching insulation spacers 4 made of glass, ceramics, etc., of which the thickness is uniform.

At the first and second glass substrates, a first pressure admitting entrance 21 of a through-hole and a second pressure admitting entrance 31 of through-hole are formed, being opposite to each other. Further, the pressure sensor 1 is connected to the first glass substrate 2 so that the pressure admitting entrance 21 is opposite to the diaphragm of the pressure sensor 1. The pressure of substance in the outside of the integrated sensor is led to the pressure sensor 1 via the pressure admitting entrances 21 and 31. The principle of detecting pressure will be explained later by referring to FIGS. 2 and 3. In the following, the composition of the integrated sensor is mainly explained.

Since the surface of the pressure sensor 1, on which the gauge resistors are not formed, is connected to the first glass substrate 2, the substance to be measured is led to the surface of the pressure sensor 1, on which the gauge resistors are not formed. Therefore, the gauge resistors, etc., do not contact the substance to be measured, so that elements arranged on the side are not contaminated.

Therefore, the deterioration of or a drift of detection characteristics of the pressure sensor can be prevented.

Furthermore, it is possible to improve corrosion-resistance by forming a passivation film on the pressure sensor 1 by using an oxidation film, a nitriding film, a Au film, a Pt film and so forth, even if the flow rate, etc., of a corrosive fluid is measured.

In the glass substrates 2 and 3, a first conductive film 23 and a second conductive film 33, made of metal and so on, are formed on two surfaces opposite to each other, respectively. Likely to the passivation of the pressure sensor 1, if the conductive film 23 and 33 on the glass substrates 2 and 3 are made of corrosion-resistant material such as Au, Pt, etc., the sensor can have the strong corrosion-resistance against acid or alkali substance. Further, if a transparent ITO (Indium Tin Oxide) film is used as the conductive films, it is possible to see the pressure sensor through the substrates, which makes it easy to produce the substrates.

If the conductive films 23 and 33 are used for electrode plates, the specific conductance or the dielectric constant of the substance between the electrode plates 23 and 33 can be measured.

In the following, the measurement principles of the specific conductance and the dielectric constant. The specific conductance σ is expressed by the following equation (1).

$$\sigma = d/(R \cdot Sef) \quad (1)$$

where d is a gap distance between the two electrode plates, Sef is an effective electrode area, and R is a resistance of liquid between the electrode plates.

Figure 24:
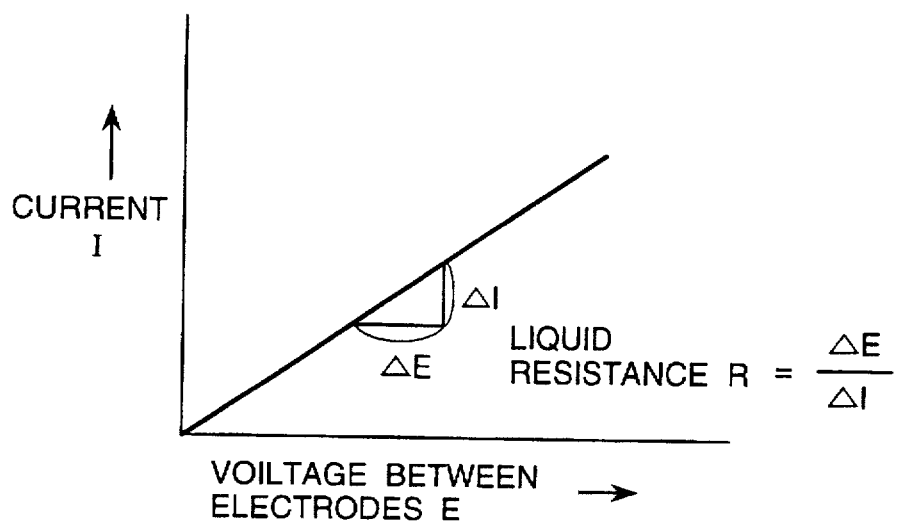
FIG. 24 is a graph showing a relation between, the voltage between the two electrode plates and current.

As shown in FIG. 24, the resistance R of liquid can be measured by the following steps of applying ΔE to the two electrodes plates 23 and 33, measuring ΔI which is current flowing between the electrodes 23 and 33 by the applied ΔE, and calculating ΔE/ΔI. Therefor, the specific conductance σ can be calculated by substituting structural parameters, namely the gap distance d and the effective electrode area Sef, of the electrode plates 23 and 33, and the measured specific conductance for the above equation (1).

Next, the dielectric constant εs is expressed by the following equation (2).

$$\epsilon s = (C/Ca) \cdot (St/Sef) - (St/Sef - 1) \quad (2)$$

where C is an electrostatic capacity for the liquid, Ca is an electrostatic capacity for air, St is a whole electrode area, and Sef is an effective electrode area contacting the liquid.

Letting ε0 a dielectric constant, the electrostatic capacity Ca is expressed by the following equation (3).

$$Ca = \epsilon_0 \cdot St/d \quad (3)$$

In the above equation (3), the electrostatic capacity Ca of air is determined by the size of the structure. Therefor, the dielectric constant of the liquid to be measured can be obtained by measuring the electrostatic constant between the electrode plates 23 and 33.

In FIG. 1, the glass substrate 2 is adhered to a hermetic terminal 5 for taking out signals from the sensor by using adhesive 18 such as epoxy resin adhesive or low melting point glass and so forth. The hermetic terminal 5 has a concave part which contains the pressure sensor 1 and form an isolation chamber for isolating the surface of the pressure sensor 1 (an surface opposite to the surface facing to the pressure admitting entrance 21) from the liquid.

Electrical signals of the pressure sensor 1 is conducted to another surface of the glass substrate 2, being opposite to the bottom surface of the glass substrate 3, by a connection wire 10 connected to the pressure sensor 1 via the conductive film 24.

That is, the top surface and the bottom surface of the glass substrate 2 are electrically connected to each other with a conductive film 24 formed on a part of the surfaces of the glass substrate 2 through the through-hole 22 so that signals of the pressure sensor 1 is conducted to the top surface of the glass substrate 2. Further, signals of the pressure sensor 1 is conducted to a pin 6 by a connection wire 11 provided at the hermetic terminal 5 from the top surface of the glass substrate 2. Furthermore, the conductive film 23 on the glass substrate 2 is electrically connected to a pin 6B provided at the hermetic terminal 5.

The conductive film 33 on the surfaces of the glass substrate 3 is electrically connected to a connection wire 11A via a through-hole 32 formed at the glass substrate 3, and the connection wire 11A is connected to a pin 6A provided at the hermetic terminal 5.

Moreover, a cap part 9 (covering member)is adhered or welded to the hermetic terminal 5 and the glass substrate 3. A space surrounded by the inside surfaces of the substrates and a surface of the hermetic terminal, etc., is filled up with silicon oil or gas so that the above-mentioned connection wires 11, 11A and 11B are isolated from the substance to be measured, and protected. In the embodiment, a differential pressure sensor is used as the pressure sensor 1.

A fluid leading path 7 (pressure leading path)is formed at the hermetic terminal 5, for admitting and leading a pressure of fluid in the outside of the integrated sensor to a surface contrary to the surface of the diaphragm, opposite to the previously-mentioned pressure admitting entrance 21. At an entrance part of the fluid leading path 7, a jointing part 8 is provided for connecting the fluid leading path 7 with an pipe in the outside of the integrated sensor. The difference between a pressure which is led and applied to the diaphragm of the pressure sensor 1 through the path 7 and a pressure applied to the diaphragm of the pressure sensor 1 via the pressure admitting entrance 31, is output as a signal proportional to the pressure difference detected by the pressure sensor 1.

Furthermore, signals corresponding to the differential pressure, the specific conductance and the dielectric constant are input to an amplifier 13 via a flexible print circuit substrate (FPC). The signals input to the amplifier 13 are input to an inputting/outputting circuit and a signal processing part 14 (microprocessor) after amplified by the amplifier 13, and each of the signals are transformed to an adequate signal form. The transformed signals are output from output terminals 16.

Power can be fed to the integrated sensor from a power source installed in the outside, or a battery 15 provided in a housing 17. In the later case, the integrated sensor can be used a very useful sensor. For example, the integrated sensor becomes portable, and can be used in the field where a power source can not be obtained.

Figure 2:
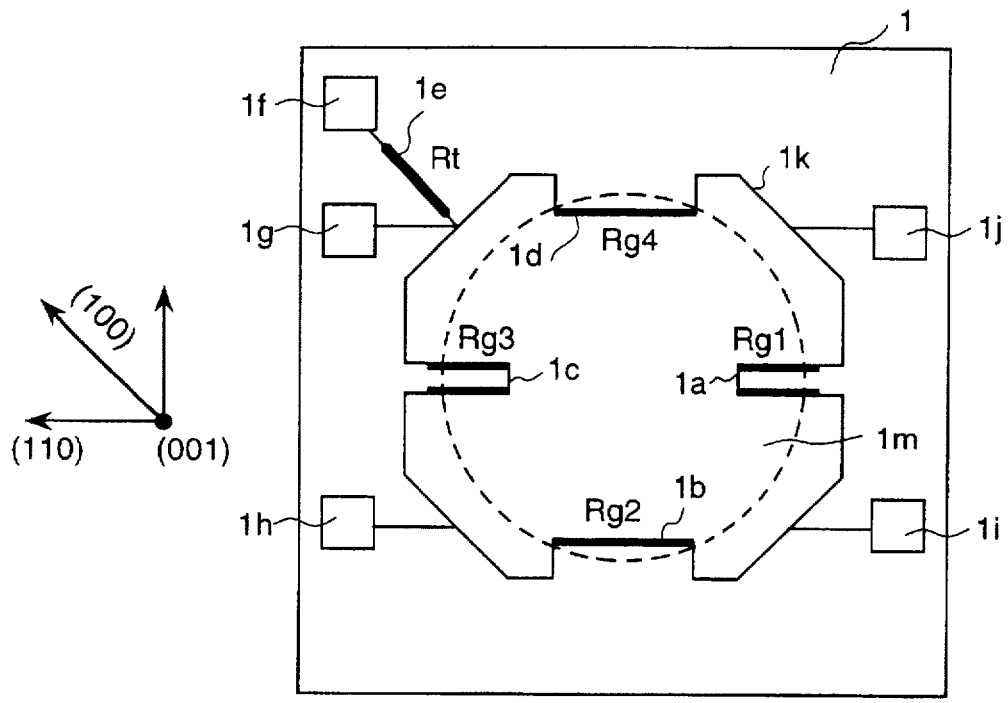
FIG. 2 is an outline composition view of pressure sensing elements and temperature sensing elements of the integrated sensor shown in FIG. 1.

FIG. 2 shows an outline composition of a piezo-resistive pressure and temperature sensor 1 used for the integrated sensor shown FIG. 1. In piezo-resistive elements 1a–1e, each of the elements being single crystal silicon formed by diffusion processing, the sensitivity to a pressure largely depends on an arrangement direction of each element (those elements have anisotropic pressure sensitivity.). If a gauge resistor (strain sensitive resistance element) formed on a (001) is oriented in the <110> direction, it has the highest sensitivity to a pressure. But, if it is oriented in the <100>, it almost has not the sensitivity to a presser. Therefore, when an element with the above-mentioned pressure sensitivity is used as a temperature gauge 1e (temperature sensitive element), it is to be arranged in the <100> direction.

In the strain gauge resistors 1a–1d orienting in the <110>, a direction of a resistance change varies, depending on whether each strain gauge resistor is oriented in the radial direction or the tangential direction of the diaphragm 1m. When a pressure is applied on the strain gauges, the resistance of each of the gauges 1a and 1c oriented in the radial direction increases, and the resistance of each of the gauges 1b and 1d oriented in the tangential direction decreases. These gauges are connected to each other with wires made of, for example, aluminum, and the wires are connected pad parts 1f–1j for taking out signals of the gauges.

Figure 3:
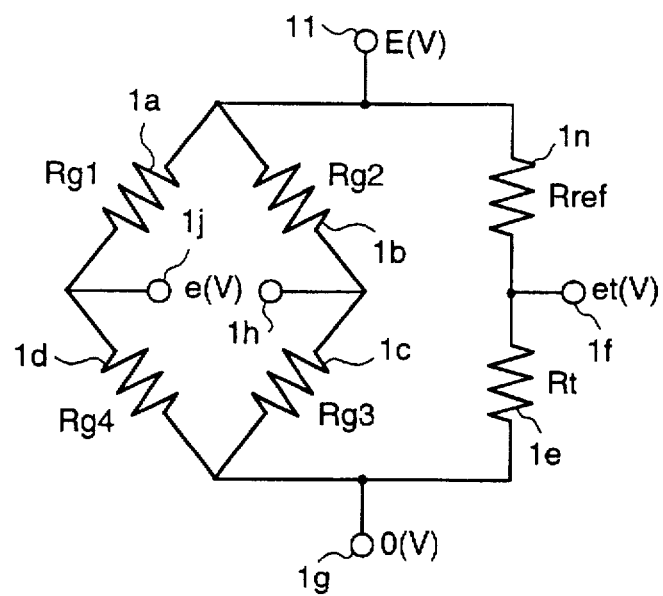
FIG. 3 shows a composition of a bridge circuit composed of gauge resistors shown in FIG. 2.
Figure 23:
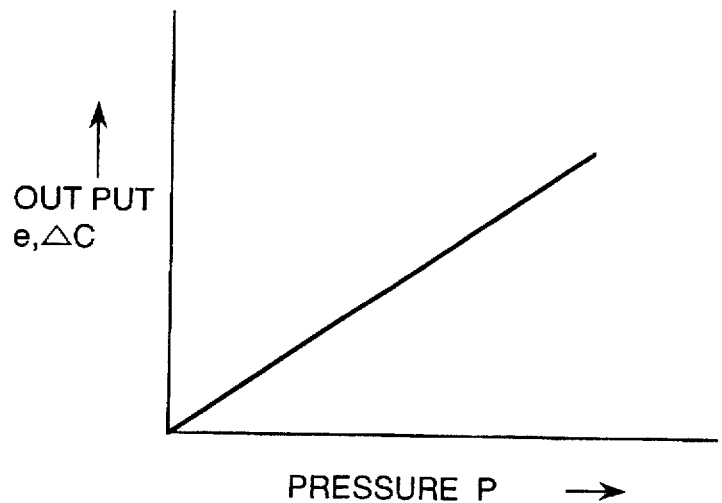
FIG. 23 is a graph showing a relation between outputs from the sensor and pressure levels.

By the above-mentioned wiring of the gauges, the gauges resistors 1a–1e compose a bridge circuit shown in FIG. 3, and an output voltage e, as shown in FIG. 23, proportional to a pressure P is obtained as a voltage between the terminal 1j and 1h by applying an exciting voltage E on the two terminals 1g and 1i.

Now, since the four gauge resistors compose the bridge circuit, temperature influences on the gauge resistors are compensated. As for temperature detection, a reference resistor 1n (Ref) of which the temperature coefficient can be neglected, is connected to the temperature gauge 1e in series, and an output voltage almost proportional to a sum of an offset voltage and a voltage corresponding to the temperature is generated at a middle point terminal 1f. By amplifying the sum voltage and subtracting the offset component from the amplified sum voltage, the temperature is obtained.

Figure 4A:
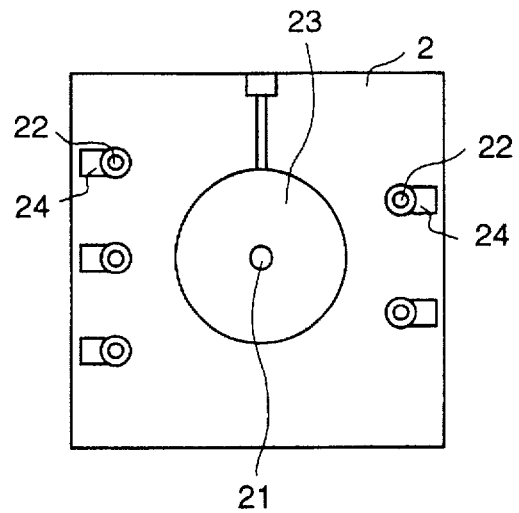
FIGS. 4(A) and 4(B) are views of a top surface and a bottom surface of a lower glass substrate shown in FIG. 1.
Figure 4B:
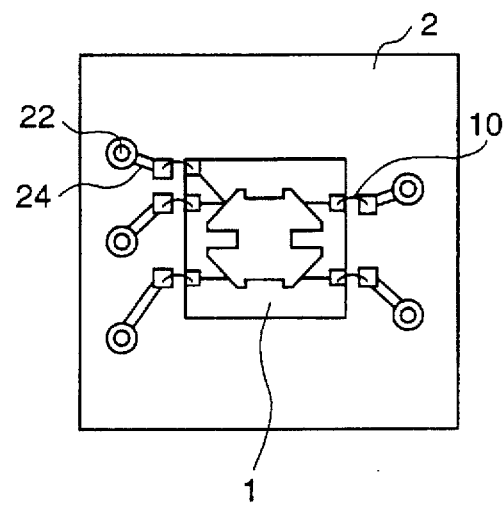

FIGS. 4(A) and 4(B) shows the top surface and the bottom surface of the glass substrate 2 shown in FIG. 1. In the figures, numeral 23 indicates the electrode plate for measuring the specific conductance and the dielectric constant, and numeral 21 indicates the pressure admitting entrance. Output signals from the pressure sensor 1 are output from the bottom surface to the top surface through the five through-holes 22 corresponding to the output pads, each through-hole conducting to the conductive film 24.

Figure 5A:
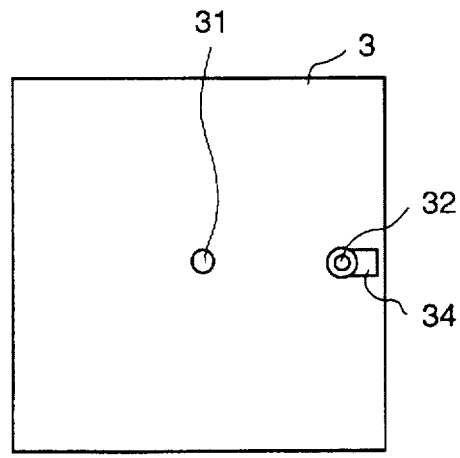
FIGS. 5(A) and 5(B) are views of a top surface and a bottom surface of an upper glass substrate shown in FIG. 1.
Figure 5B:
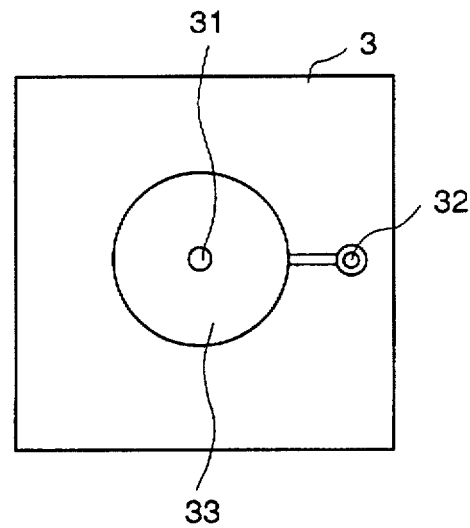

FIGS. 5(A) and 5(B) shows the top surface and the bottom surface of the glass substrate 3 shown in FIG. 1. In the figures, numeral 31 indicates the pressure admitting entrance, numeral 33 indicates the electrode plate for measuring the specific conductance and the dielectric constant. The electrode plate 33 is electrically connected to the conductive film on the top surface via the through-hole 32.

As mentioned above, in the first embodiment, since the conductive films opposite to each other are provided for forming a space between the conductive films, filled with the liquid to be measured, so as to measure the specific conductance and the dielectric constant of the liquid, connected to the liquid admitting path for leading the substance to the diaphragm for measuring a differential pressure detected by the pressure sensor 1, it is possible to realize the integrated sensor capable of a water quality and a differential pressure (flow rate) with only one sensor.

Figure 6:
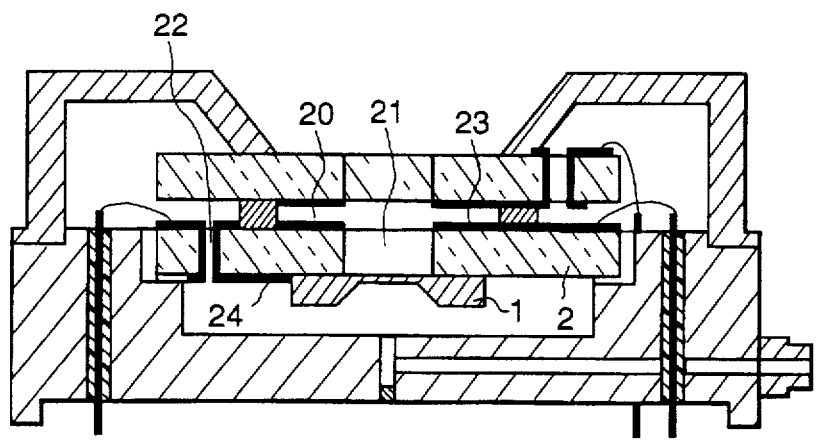
FIG. 6 is an outline sectional view of an integrated sensor of a second embodiment according to the present invention.
Figure 7:
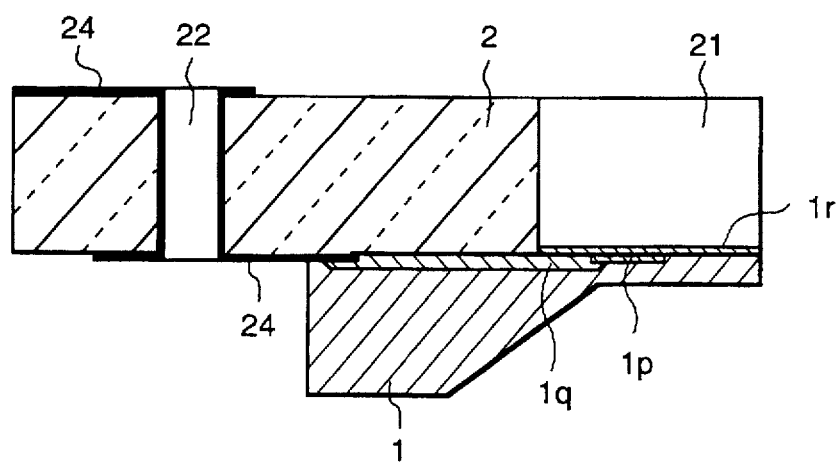
FIG. 7 is an enlarged view of a main part of the sensor shown in FIG. 6.

FIGS. 6 and 7 is an outline composition sectional view and an outline sectional view of a main part, of an integrated sensor of the second embodiment according to the present invention.

In the second embodiment, a surface on which the pressure and temperature sensor 1 is composed of piezoresistors, is directly connected to the bottom side of the glass substrate 2. Since a surface (gauge circuit forming surface) on which, for example, five gauges are arranged, should be flat in order to directly connect the surface to the glass substrate 2, the wire k of the pressure sensor 1, and the pads 1f–1j can not be made of aluminum.

To solve the problem, a low resistance diffused layer 1q (p+ layer) is formed and inserted between the surface of the pressure sensor 1 and the glass substrate 2 together with the conductive film 24, which composes an anodic bonding. Since the above-mentioned structure forms the ohmic contact, signals can be taken in from the electrode without wiring connection. But, since the gauge forming surface directly contacts the liquid to be measured, the gauge circuit surface has to be passivated with an isolation film such as an oxidation film, a nitriding film, or a multi-layer film 1r made by laminating a Au film or a Pt film on the above-mentioned isolation film.

The second embodiment has the same effects as the first embodiment. Moreover, since the pressure sensor has no wiring connection on its surface, it is possible to reduces production processing steps, and to improve the yield of the integrated sensors since a misoperation of cutting the connection wire 10 can not occur in the processing of adhering the hermetic terminal 5 to the glass substrate.

Figure 8:
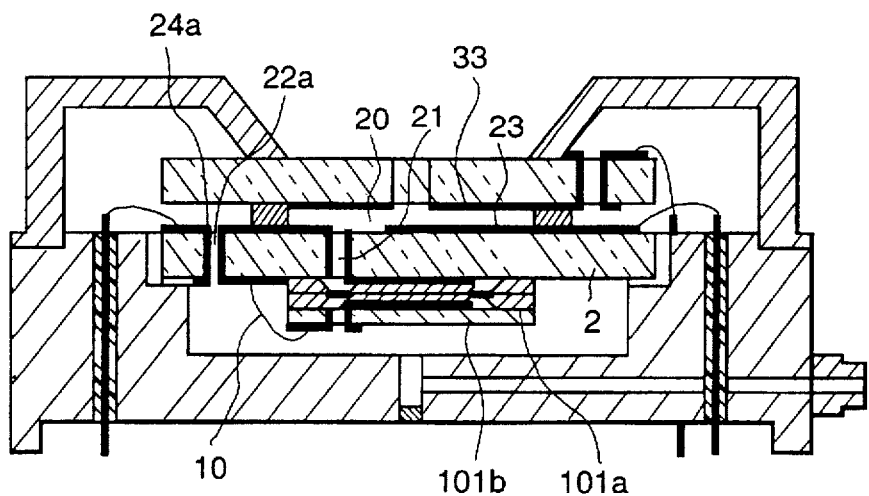
FIG. 8 is an outline sectional view of an integrated sensor of a third embodiment according to the present invention.
Figure 9:
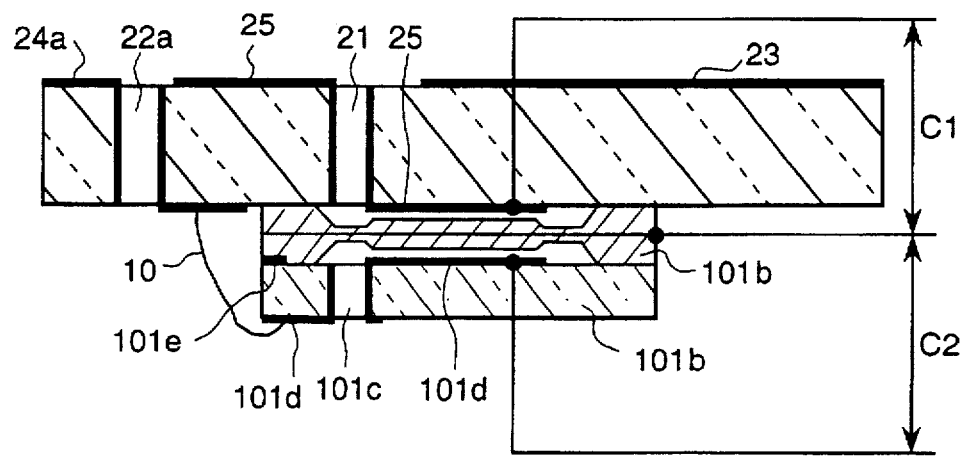
FIG. 9 is an enlarged view of a main part of the sensor shown in FIG. 8.

FIGS. 8 and 9 is an outline composition sectional view and an outline sectional view of a main part, of an integrated sensor of the third embodiment according to the present invention.

In the third embodiment, an electrostatic capacitance sensor is used for the pressure sensor. In the figures, the glass substrate 2 in which an upper fixed electrode 25 is provided, is connected by the anodic bonding to a substrate 101b made of boro-silicated glass, etc., a movable electrode 101a made of single crystal silicon being provided between the glass substrate 2 and the substrate 101b.

A boss is formed at the central part of the movable electrode 101a by etching processing, and each of a gap between the boss and the substrate 2, and a gap between the boss and the substrate 101b is a distance of microns–tens of microns. At the substrate 101b, a small through-hole 101c for leading a pressure to the movable electrode 110a from the under side of the substrate 101b, and an fixed electrode 101d is formed on the top and bottom surfaces of the substrate 101b via the through-hole 101c.

Pressure measuring in the third embodiment is explained as follows.

The movable electrode 110a displaces, in proportion to a difference between of two levels the pressure led to both side of the movable electrode 110a via the pressure admitting entrance 21 and 101c. In proportion to the amount of the displacement of the movable electrode 101a, the electrostatic capacitance difference ΔC (C1–C2) is generated, where C1 is an electrostatic capacitance between the upper fixed electrode 25 and the movable electrode 101a, and C2 is an electrostatic capacitance between the lower fixed electrode 110d and the movable electrode 101a.

Therefore, since the electrostatic capacitance difference ΔC (C1–C2) is proportional to the pressure difference as shown in FIG. 23, the generated presser difference can be obtained. Although the electrostatic capacitance type pressure sensor has a structure more complicated than the piezo resistor type pressure sensor, since this type pressure sensor has the low sensitivity to the temperature, the electrostatic capacitance type pressure sensor can be used in a wider temperature range.

Further, current almost does not flow between the electrode 25 and the electrode 101d, which considerably reduces power to be consumed.

Figure 10A:
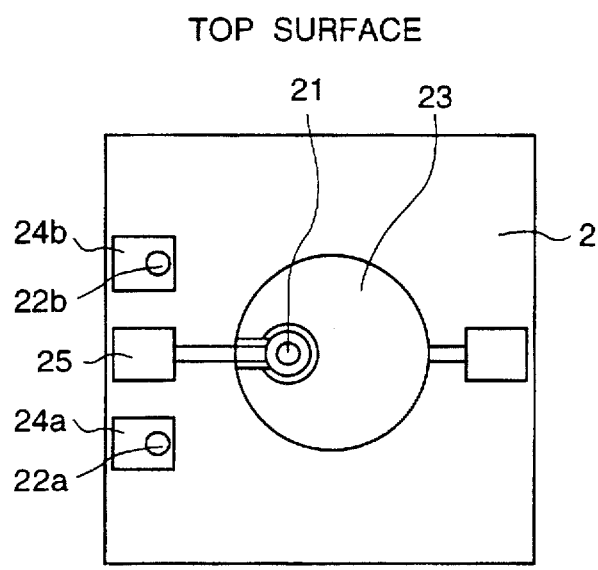
FIGS. 10(A) and 10(B) are views of a top surface and a bottom surface of a lower substrate shown in FIG. 8.
Figure 10B:
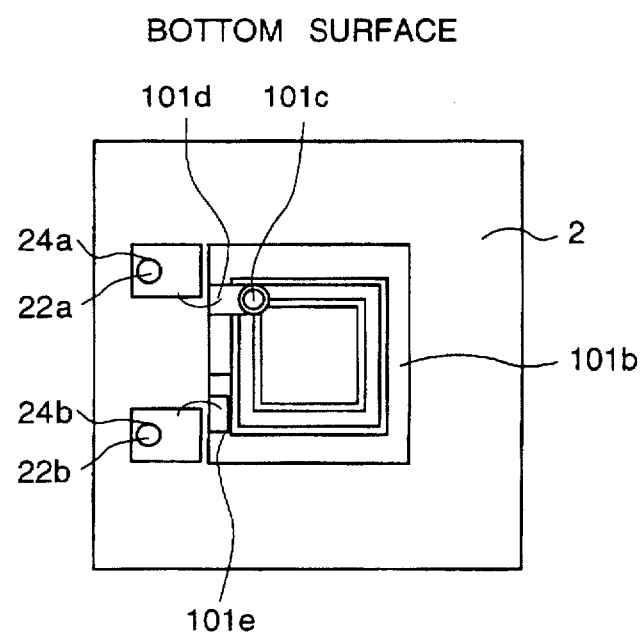

FIGS. 10(A) and 10(B) show the top surface (FIG. 10(A)) and the bottom surface (FIG. 10(B)).

In the figures, numeral 21 indicates the pressure admitting entrance, and numeral 23 indicates the electrode used for measuring the specific conductance and the dielectric constant. Further, numeral 25 indicates the upper fixed electrode and its pad, and numerals 22a and 24a indicate the through-holes for leading out the voltage signal of the lower fixed electrode 101d and its electrode pad. Moreover, a notch is formed at the substrate 101b by which a part of the movable electrode 101a is exposed in the direction of a back surface of a paper on which FIG. 10(B) is illustrated, via the substrate 101b, in order to lead out the voltage of the movable electrode 101a. An electrode pad 101e made of aluminum, etc., is formed at a part of the exposed part of the movable electrode 101a, and connected to an electrode pad 24b. The electrode 101e is connected to an electrode pad 24b by a wire via a through-hole 22b for leading out a signal to the outside.

By realizing the above-mentioned sensor composition, the electrostatic capacitance C1 between the electrode 25 and the movable electrode 101a can be obtained by measuring the electrostatic capacitance between the electrode 25 and the electrode pad 24b, and the electrostatic capacitance C2 between the electrode pad 101d and the movable electrode 101a can be obtained by measuring the electrostatic capacitance between the electrode pad 24a and the electrode pad 24b. Further, the difference of electrostatic capacitance ΔC between the measured electrostatic capacitance's C1 and C2 is calculated, and the pressure to be measured is obtained, based on the calculated difference of electrostatic capacitance ΔC.

As mentioned above, the third embodiment has the similar effects as the second embodiment, according to the present invention. Further, an electrostatic capacitance type sensor is also used as the presser sensor, and can be used in a wide temperature range, since the pressure sensor of this embodiment has the low sensitivity to temperature changes since. Furthermore, current almost does not flow between the electrode 25 and the electrode 101d, which considerably reduces power to be consumed.

Figure 11:
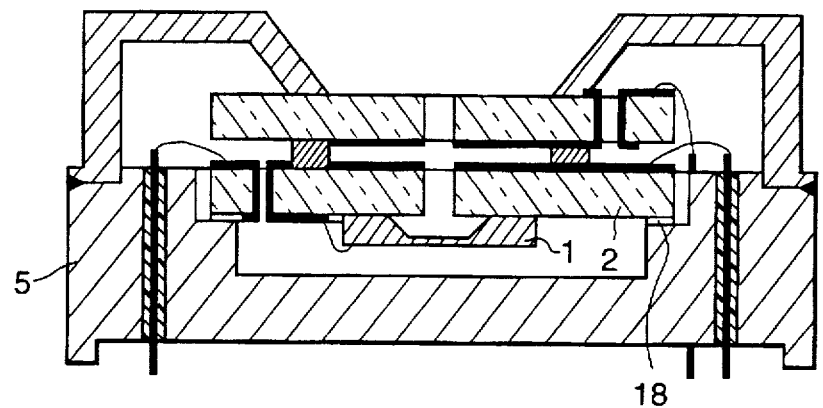
FIG. 11 is an outline sectional view of an integrated sensor of a fourth embodiment according to the present invention.

FIGS. 11 is an outline composition sectional view of the integrated sensor of the fourth embodiment according to the present invention. In the fourth embodiment, a piezo-resistive absolute pressure sensor and a sensor for measuring the specific conductance and the dielectric constant are integrated into one presser sensor.

That is, in this embodiment, although the pressure sensor itself is also a differential pressure sensor, a liquid leading path such as the leading path 7 shown in FIG. 1 is not provided in the hermetic terminal 5, and the pressure of the outside substance to be measured is not led to another surface of the diaphragm of the pressure sensor 1. The integrated sensor of this embodiment has the same structure as the first embodiment shown in FIG. 1 other than the liquid leading path 7.

A space containing the another surface of the diaphragm of the above-mentioned pressure sensor is isolated from the outside by a adhering member, and kept airtight at about 1 atmospheric pressure.

Therefore, in the fourth embodiment, since the presser at the space containing the another surface of the presser sensor is known as almost 1 atmospheric pressure, the absolute outside pressure can be obtained, based on the differential pressure measured by the pressure sensor 1. Thus, it is possible to provide the integrated sensor capable of simultaneously measuring the absolute pressure, the specific conductance and the dielectric constant.

Figure 12:
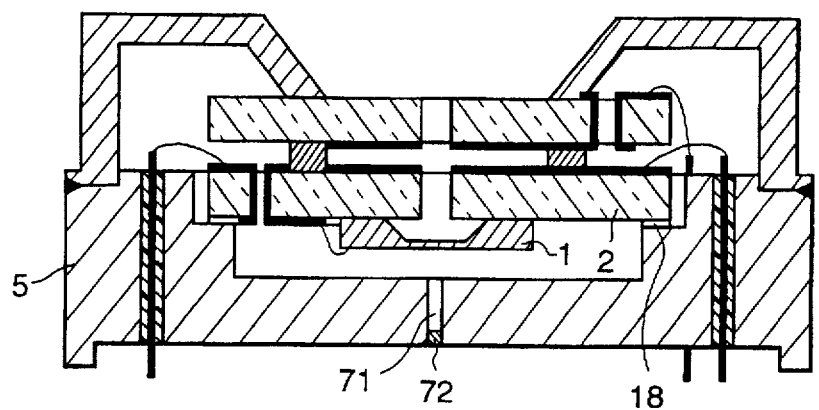
FIG. 12 is an outline sectional view of an integrated sensor of a fifth embodiment according to the present invention.

FIG. 12 is an outline composition sectional view of a main part of the integrated sensor of the fifth embodiment according to the present invention. In the fifth embodiment, a piezo-resistive vacuum sensor and a sensor for measuring the specific conductance and the dielectric constant are integrated into one presser sensor.

That is, the pressure sensor 1 of this embodiment is suitable to the case in that the pressure of the substance to be measured has a low level, for example, 100 mm Torr. The space, formed in the hermetic terminal, containing another surface of the diaphragm of the pressure sensor 1 is kept as an almost vacuum space.

In order to prepare the above-mentioned vacuum space, a fluid leading path 71 communicating with the outside is formed in the hermetic terminal 5, and the above-mentioned space formed in the hermetic terminal 5 is depressurized to the predetermined vacuum level by using the fluid leading path 71. Further, when the predetermined vacuum level of the space in the hermetic terminal 5 is attained, the space is kept at a vacuum state by closing the fluid leading path 71 by a plug 72.

The structure of the integrated sensor shown in FIG. 12 is the same as the structure shown in FIG. 1, except that the fluid leading path 71 is formed in place of the path 7, and the path 71 is closed with the plug 72.

The fifth embodiment can realize to provide an integrated sensor capable of simultaneously measuring the presser, the specific conductance and the dielectric constant of the low pressure substance.

FIGS. 13–17 are figures for explaining a production method of the integrated sensor of the first embodiment shown in FIG. 1.

Figure 13:
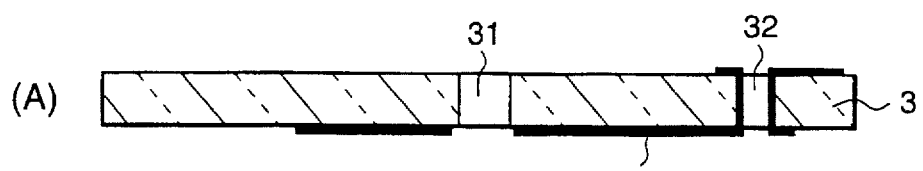
FIGS. 13(A) and 13(B) are sectional views for explaining a production method of the integrated sensor of the first embodiment.

At first, in a process shown in (A) of FIG. 13, the pressure admitting entrance 31 and the through-hole 32 are formed at the substrate 3. Next, at both surfaces of the substrates 3, the corrosion-resistive conductive films 33 of the predetermined patterns is formed with corrosion-resistive material such as Au, Pt and so on, by a evaporation deposition method, a spattering method, a plating method, etc. In a process shown in (B) of FIG. 13, the pressure admitting entrance 21 and the through-hole 22 and the conductive films 23 and 4 are formed at the substrate 2, likely to the process (A) for the substrate 2.

Figure 14:
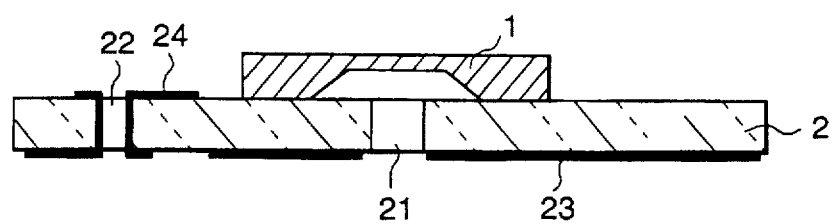
FIG. 14 is a sectional view for explaining a production method of the integrated sensor of the first embodiment.

Further, as shown in FIG. 14, the substrate 2 and the pressure sensor 1 is heated at the temperature 300°–350° C., and both articles are connected by applying the voltage of about 1 kV (anodic-bonding) to the articles.

Figure 15:
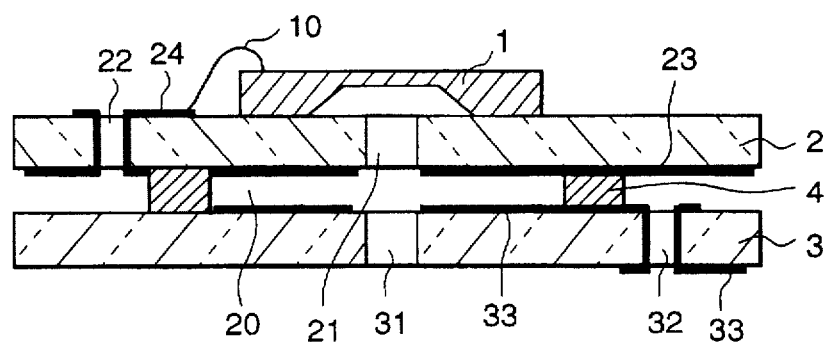
FIG. 15 is a sectional view for explaining a production method of the integrated sensor of the first embodiment.

As shown in FIG. 15, a spacer 4 made of insulating material such as glass, ceramics, etc. is inserted between the substrates 2 and 3, and bonded to the substrates. Further, the pressure sensor 1 is connected to the conductive film 24 with the connection wire 10.

Figure 16:
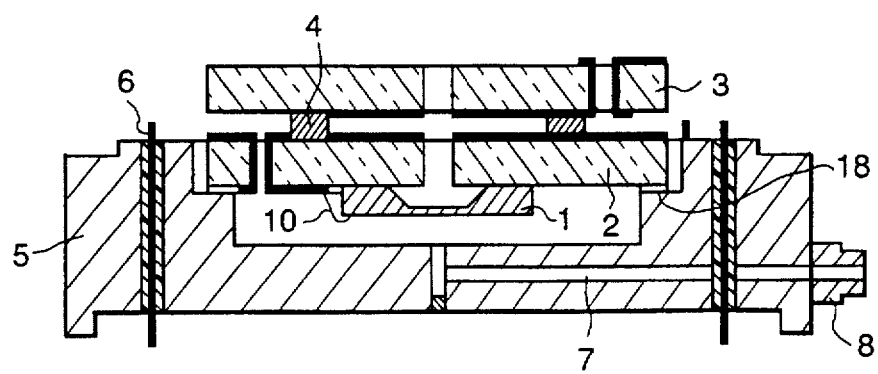
FIG. 16 is a sectional view for explaining a production method of the integrated sensor of the first embodiment.

Further, as shown in FIG. 16, the composition state in which the substrates 2 and 3, the pressure sensor, etc., are combined, is upset in the paper illustrating FIG. 16, and the hermetic terminal 5 (a sealing member having a concave part and connection terminals) is connected to the substrate 2 with adhesive material 18 such as epoxy resin adhesive.

Figure 17:
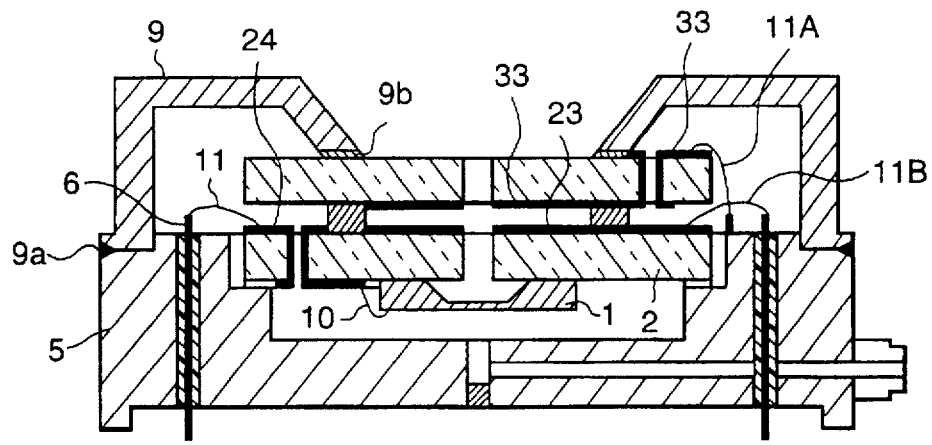
FIG. 17 is a sectional view for explaining a production method of the integrated sensor of the first embodiment.

At last, as shown in FIG. 17, the connection wires 11, 11A and 11B are connected to the pin 6 and the conductive film 24, the conductive film 34, and the conductive film 23, respectively, and the cap 9 is welded to the hermetic terminal 5 (9a: welded part), and adhered to the substrate 3 (9b: adhered part). Each integrated sensor of the embodiment shown in FIG. 6, FIG. 8, FIG. 11 or FIG. 12, is produced by similar processing such as the production processing shown in FIGS. 13–17, of the integrated sensor shown in FIG. 1.

Although, in the above-explained embodiments, the substrate 3 is made of insulating material, it is possible to use metal (conductive material) for the substrate 3.

Figure 18:
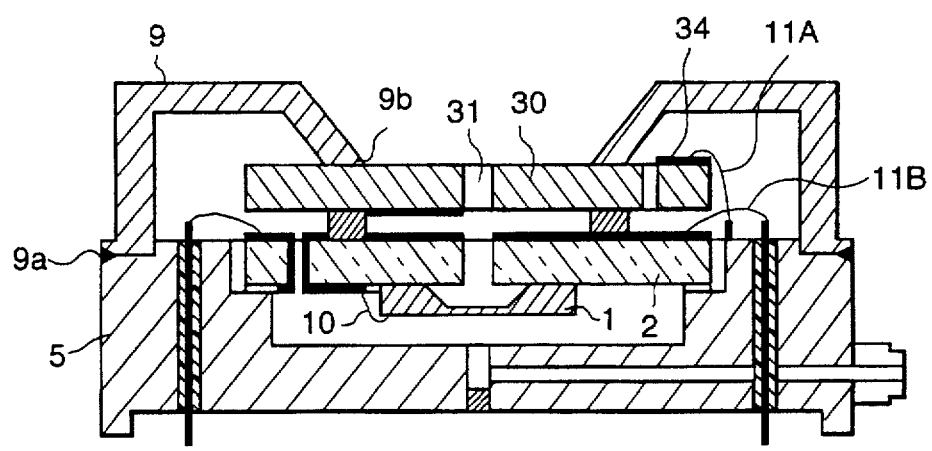
FIG. 18 is an outline sectional view of an integrated sensor of a sixth embodiment according to the present invention.

FIG. 18 is an outline composition sectional view of a main part of an integrated sensor devised as the sixth embodiment according to the present invention, in which the upper substrate is a metal substrate 30. Since the substrate 30 is made of metal, and the substrate 30 itself can function as an electrode without forming a conducive film on the surface of the substrate 30, the structure of the integrated sensor becomes simple. However, it is necessary to form a bonding pad 3-34 at a part of the substrate 30, for connecting the substrate 30 to the pin of the hermetic terminal 5.

Further, since the cap 9 can be directly welded to the metal substrate 30 via the welded part 9b, and the connection between the cap 9 and the substrate 30 has the higher temperature resistance, the reliability of the connection between the cap 9 and the substrate 30 can be improved, in comparison with the connection method using adhesive.

The sixth embodiment has the same effects as the first embodiment, and the structure of the integrated becomes simpler.

Now, if the using environment of the integrated sensor hardly oxidizes the substrate 30, usual metal such as copper. On the other hand, if the using environment of the integrated sensor easily corrodes metal, rare metal such as Au, Pt, etc., is to be used for the substrates 30.

Figure 19:
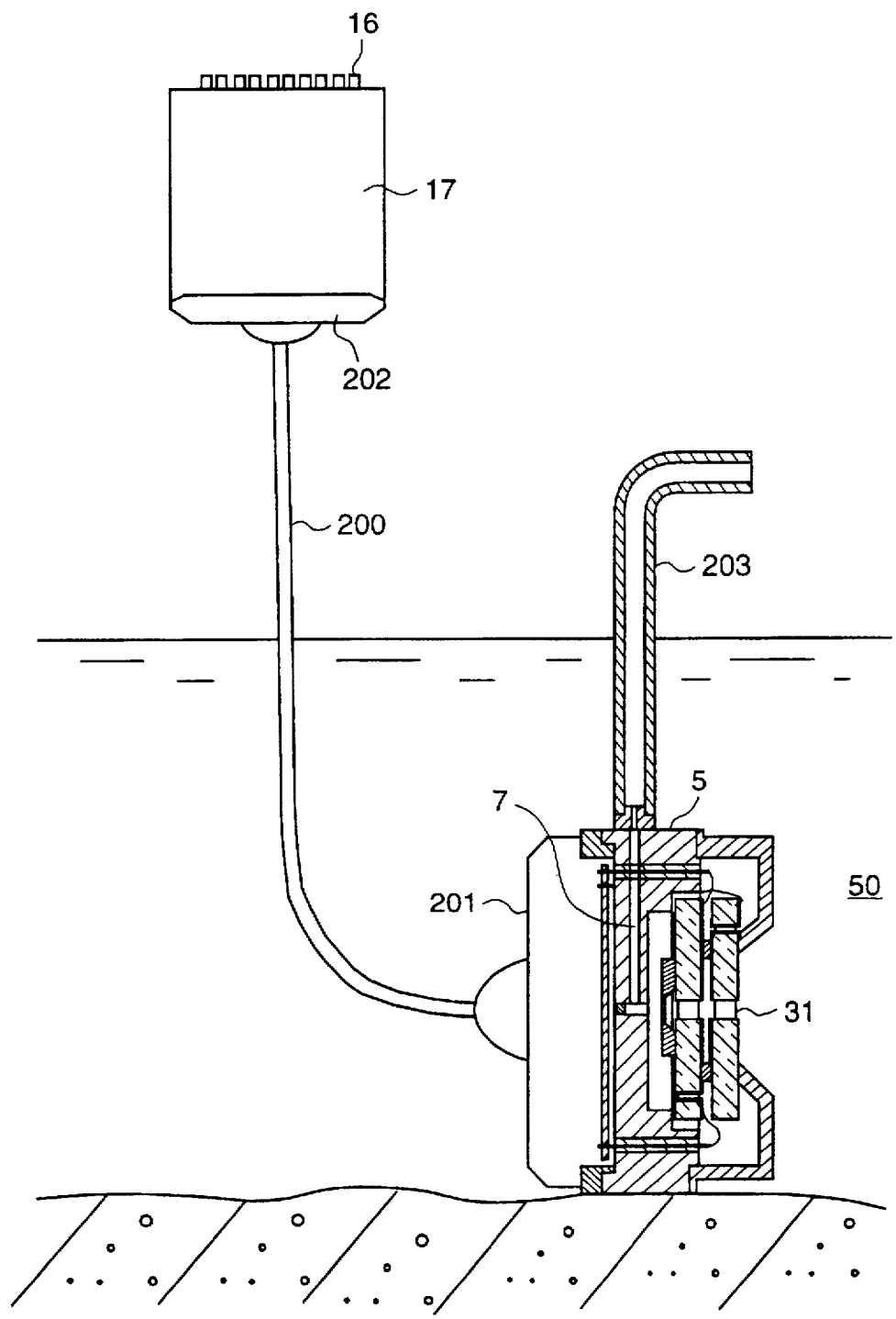
FIG. 19 is an illustration for showing an example case in which the integrated sensor of the present invention is used as a water level detector with a water quality monitoring function.

FIG. 19 shows an example case in which the integrated sensor for measuring a water level and a water quality is used as a water level sensor with a water quality monitoring function. In the case, the water quality is monitored by detecting the specific conductance of an object liquid to be measured.

In FIG. 19, the above-mentioned water level detector is separated into a sensor part 50 and a signal processing part contained in a housing 17. The sensor part 50 is positioned at the bottom of the water, and the signal processing part contained in a housing 17 is positioned in the atmosphere. The sensor part 50 is electrically connected to the signal processing part contained in a housing 17 by using a water-proofing transmission line 200, and adapters 201 and 202. By adopting the above-mentioned arrangement, water can be prevented from intruding into the signal processing part. Further, since input/output terminals to be connected to outside equipment are also positioned in air, wiring for the connection of the outside equipment and the input/output terminals becomes easy.

If the water-proofing transmission line 200 is long, and the attenuation of a signal in the transmission line 200 is large, an amplifier is provided in the adapter 201.

Moreover, if the fluid pressure leading path 7 is closed, influences of changes in the air pressures on changes of the detected water level can not be removed, which cause measurement errors. In order to solve the above-mentioned problem, a pipe 203 is connected to the fluid pressure leading path 7, and is projected in air. When the above-mentioned integrated sensor is used in the outside of a house, intruding of rain into the pipe 203 has to be taken into account. In the case shown in FIG. 19, the intruding of rain into the pipe 203 is prevented by bending the top part of the pipe 203 in the horizontal direction or toward to a water surface.

Figure 20:
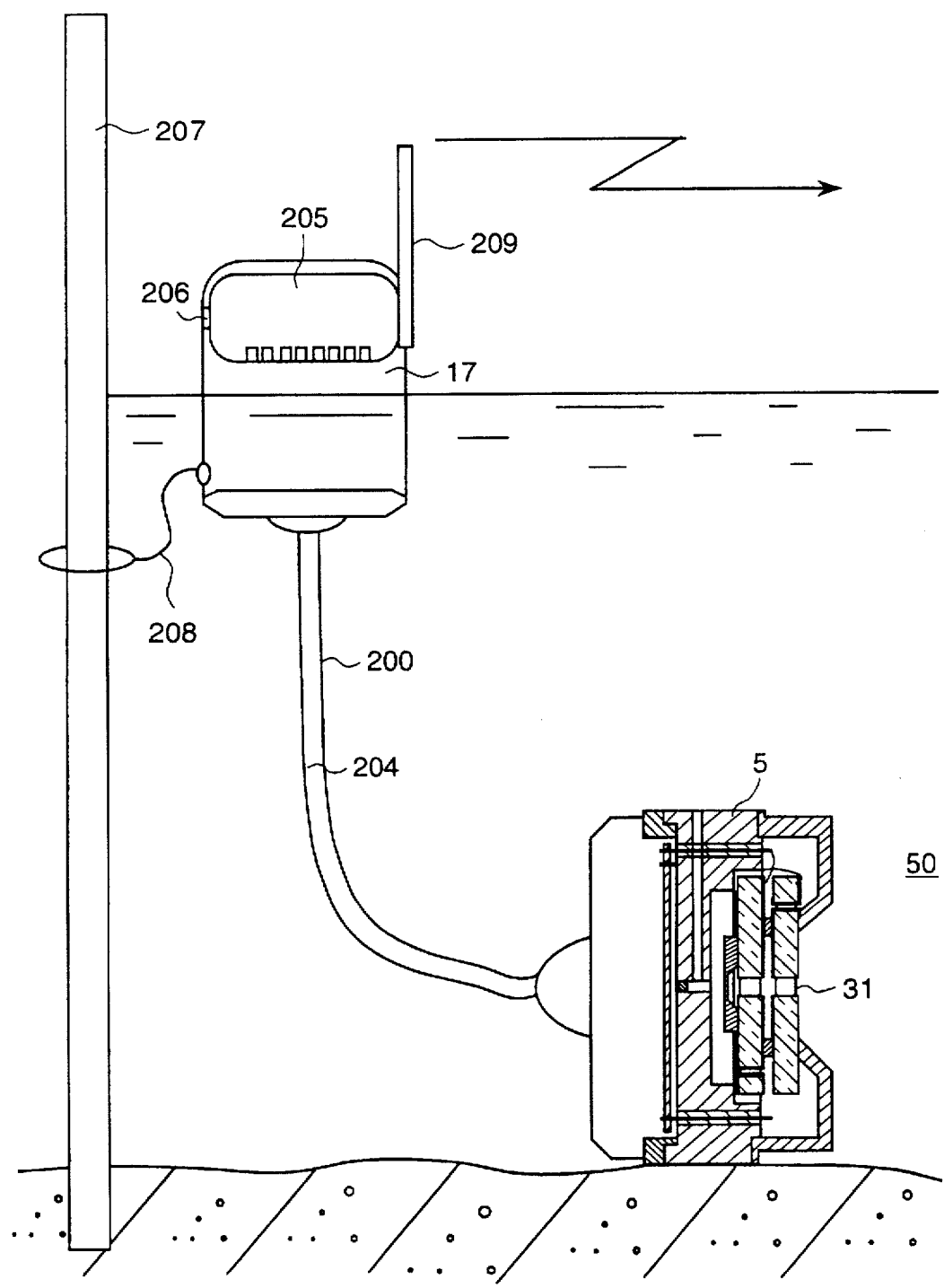
FIG. 20 is an illustration for showing another example case in which the integrated sensor of the present invention is used as a water level detector with a water quality monitoring function.

FIG. 20 shows another example case in which the integrated sensor for measuring a water level and a water quality is used as a water level sensor with a water quality monitoring function.

Likely to the case shown in FIG. 19, the sensor part 50 and the housing 17 is separately arranged each other. In this case, an air chamber 205 is provided at the housing 17. The air chamber 205 supports the housing 17 to float on a water surface. By using the above-mentioned arrangement or composition of the integrated sensor, it is possible to keep the position of the housing 17 on a water surface without manually adjusting the position of the signal processing part contained in the housing 17 even when the level of water violently changes.

Furthermore, in order to prevent the housing 17 from largely displacing, a support pole is installed, and a small part 208 having a small friction property in the vertical direction such as a ring is passed through the support pole 207. The housing 17 is connected to the small part 208. Likely to the case shown in FIG. 19, in order to remove the influences of changes in the atmospheric pressure, a space containing another surface of the diaphragm has to be led to the atmosphere.

In this case, an atmospheric pressure leading path 204 is provided in the water-proofing signal transmission line 200 for connecting the sensor part 50 and the housing 17, and an aperture is formed at a part of the housing 17.

Therefore, in the above-mentioned arrangement or composition in using the integrated sensor, it is possible to lead the atmospheric presser to the sensor part 50 without providing the special pipe 203 needed in the case shown in FIG. 19.

In the case that the object substance to be measured is located at a long distance place apart from a monitoring room, a usual battery or a solar battery is loaded as power source in the housing 17. Further, an antenna 209 is provided at the housing 17, and signals detected by the sensor part 50, etc., can be transmitted by wireless to the monitoring room by using the antenna 209.

Figure 21:
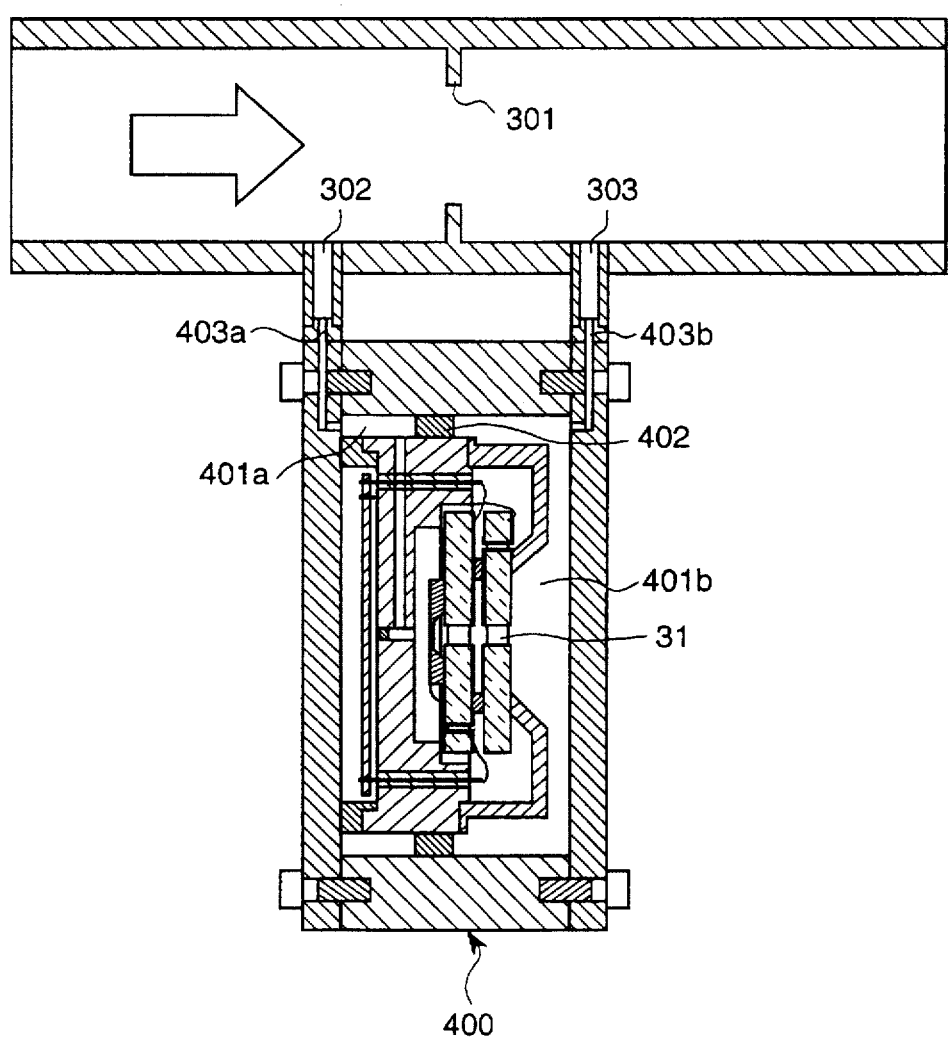
FIG. 21 is an illustration for showing an example case in which the integrated sensor of the present invention is used as a flow rate detector with a water quality monitoring function.

FIG. 21 shows another example case in which the integrated sensor for measuring a flow rate and a water quality is used as a flowmeter with a water quality monitoring function. In the case shown in FIG. 21, the quality of the fluid to be measured is monitored by measuring the specific conductance of the fluid.

In FIG. 21, at a position of a pipe-line 300 in which the fluid to be measured flows in the direction of an arrow shown in FIG. 21, an orifice 301 is provided at a place of the pipe-line 300, the pressure difference (differential pressure) is generated between the pressure in the upper stream and the pressure in the lower stream, of the orifice. Since the volume flow rate of the fluid is proportional to ½ factorial of the differential pressure, the volume flow rate can be obtained, based on the measured differential pressure before and after the orifice (by the principle of a differential pressure volume flowmeter).

In the industrial instrumentation field, since the very high pressure, for example, hundreds of atoms, has to be sometimes measured, the differential pressure sensor and the specific conductance sensor are provided in and welded to a strong housing 400. The inside space of the housing 400 is divided into a high presser room 401a and a low pressure room 401b by a flange 402.

The pressure in the upper stream of the orifice 301 is taken in from a port 302 of the pipe-line 300, and led to the high pressure room 401a via a pressure admitting entrance 403a. Further, the pressure in the lower stream of the orifice 301 is taken in from a port 303 of the pipeline 300, and led to the low pressure room 401b via a pressure admitting entrance 403b.

Although not shown in the figure, the signal processing unit is arranged in the direction vertical to the paper showing the figure, in the housing 400. The integrated sensor shown in FIG. 21 can measure the flow rate of the fluid flowing in the pipe-line 300, and can detect changes of the composition of the fluid if the fluid is electrolytic liquid, besides the late of water, since the integrated sensor also measures the specific conductance.

Figure 22:
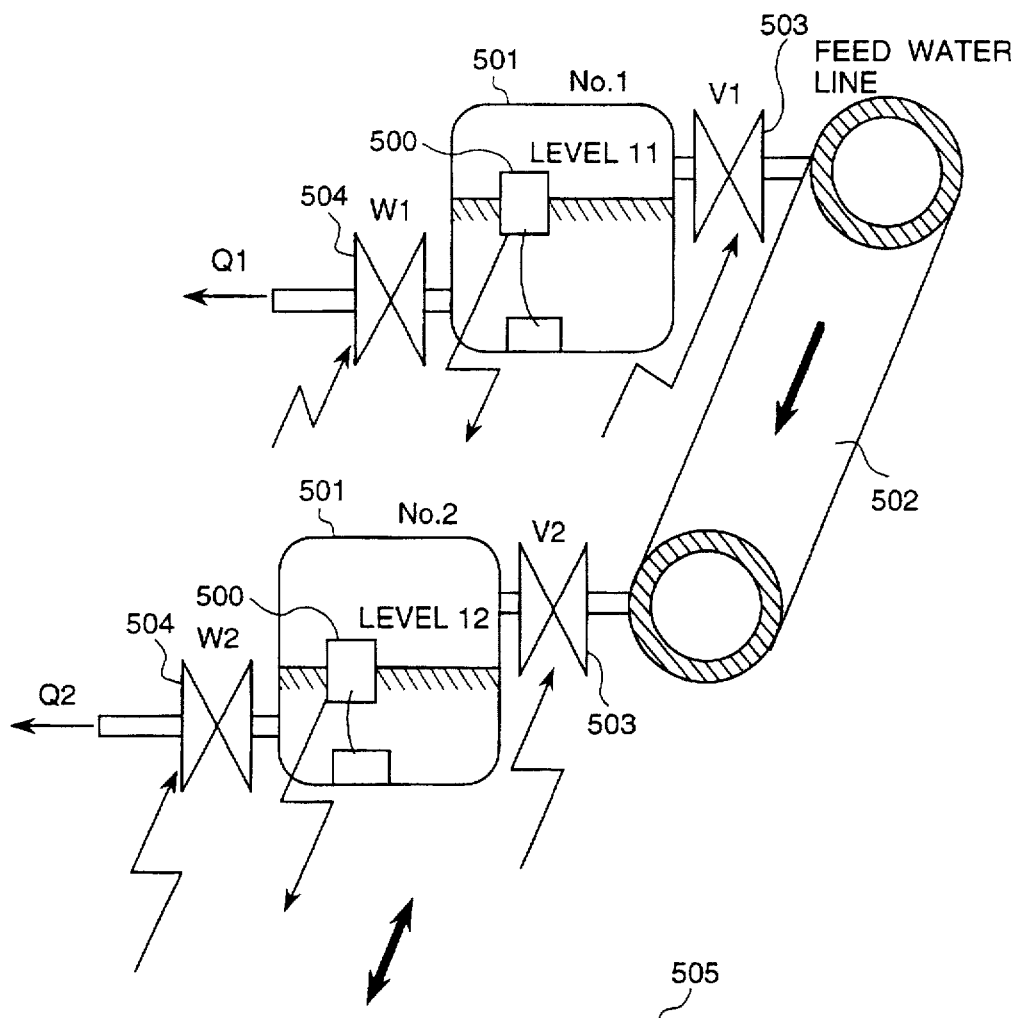
FIG. 22 illustrates an example of a fluid management system using the integrated sensor of the present invention.

FIG. 22 is a typical illustration of a fluid management system using the integrated sensor of the present invention.

In the case shown in FIG. 22, a plurality of pools are connected to a feed- water line 502, and each pool is composed of a pooling part 501, a feed-water valve (V1, V2) and a drain-water valve (W1, W2).

Signals of the level, the temperature and the specific conductance measured by the integrated sensor provided at each pool are transmitted to a control system in a control room. The control systems controls the openings of the feed-water valve 503 and the drain-water valve 504 according to the following processes (A), (B) and (C).

(A) If the temperature and the specific conductance of the water to be measured, the i-th pool 501 are within predetermined ranges, respectively, the water level is adjusted within a predetermined range. In the water level adjustment, if the water level of the i-th pool reaches the upper limit height, the feed-water valve Vi is closed and the drain-water valve Wi is opened. Further, if the water level if the i-th pool reaches the lower limit height, the feed-water valve Vi is opened and the drain-water valve Wi is closed.

(B) If the specific conductance of the water in the i-th pool is out of a predetermined range, an alarm is generated in the control room, and the water quality deterioration occurring pool, the occurring time and the deterioration grade of the deterioration are informed to an operator. In order to prevent the deteriorated quality water from flowing to the outside, the feed-water valve Vi and the drain-water valve Wi are closed.

(C) If the temperature of the water in the i-th pool is out of a predetermined range, an alarm is generated in the control room, and the anomalous temperature occurring in the pool, the occurring time and the anomalous temperature are informed to an operator. If it is determined that the anomalous temperature gives bad influences on the fluid management system, the feed-water valve Vi and the drain-water valve Wi are closed.

As explained above, if the integrated sensor is applied to a fluid management system, operations and management of the system becomes easier since it is possible to measure a water level, a temperature and a water quality by using one sensor for each pool. Further, it becomes also easier to install a sensor for each pool and provide transmission wires between a fluid control room and pools.

The above-mentioned fluid management system can be applied to a water filtration plant. Although an existing water filtration plant performs a process of mixing chlorine with water and a pasteurizing process, if the amount of mixed chlorine is too much, the problem in which the quality of water becomes the state generating chlorine smell, is caused. Therefore, by applying the integrated sensor of the present invention to a water filtration plant, since it is possible to measure a water level, a temperature and a water quality by using one sensor, an improved water filtration plant can be realized, in which operations and management of the plant becomes easier, and it becomes also easier to install a sensor for each pool and provide transmission wires between a fluid control room and pools in the plant.

Since the integrated sensor of the present invention has the composition such as mentioned above, the following effects of the sensor can be expected. Since the integrated sensor, comprises a first substrate connected to the diaphragm, possessing, the pressure led to the diaphragm via a first pressure admitting entrance for admitting the pressure of the substance to be measured and a first conductive film thereon, the pressure led to the diaphragm via a second substrate possessing a second pressure admitting entrance for admitting the pressure of the substance to be measured, via the first pressure admitting entrance, and a second conductive film, and a signal processing unit for measuring the specific conductance and the dielectric constant of the substance filled between the first conductive film and the second conductive film, and the differential pressure of the substance, by using output signals transmitted from the pressure sensor, it is possible to realize an integrated capable of simultaneously measuring a water level and a water quality, or a water flow rate and a water quality by one sensor for each one of paddy fields or a water pooling system.

Moreover, if a temperature-sensitive element is also integrated into the above-mentioned integrated sensor, an integrated sensor is realized and provided, by which the temperature of water can be measured besides a water level and a water quality, and a water flow rate and a water quality, by one sensor.

A fluid management system consisting of pooling parts for storing fluid, a fluid feeding part for inputting fluid into each pooling part, a fluid draining part for outputting fluid from each pooling part, and a control part for adjusting the level of fluid in each pooling part, is composed so that the integrated sensor of the present invention is provided at each pooling part, a fluid quality of each pooling part is monitored by measuring the specific conductance, and an alarm is generated if the measured specific conductance is out of a predetermined range.

Furthermore, by applying the integrated sensor of the present invention to a water management system, since it is possible to measure a water level, a temperature and a water quality by using one sensor, an improved water management system can be realized, in which operations and management of the system becomes easier, and it becomes also easier to install a sensor for each pool and provide transmission wires between a fluid control room and pools in the system.

What is claimed is:

1. An integrated sensor, comprising:
   a pressure sensor including a diaphragm displacing corresponding to a pressure of an object substance to be measured;
   a first substrate connected to said diaphragm, possessing a first pressure admitting entrance for leading said pressure of said substance to be measured, to said diaphragm, and a first conductive film formed on said first substrate;
   a second substrate possessing a second pressure admitting entrance for leading said pressure of said substance to be measured, to said diaphragm via said first pressure admitting entrance, and a second conductive film at a position facing to said first conductive film, which is separated with a predetermined interval; and
   a signal processing unit for measuring at least one of a specific conductance and a dielectric constant of said substance filled between said first conductive film and said second conductive film, and said pressure of said substance, by using output signals transmitted from said pressure sensor.

2. An integrated sensor according to claim 1, wherein said diaphragm in said pressure sensor is made of single crystal silicon, at which a temperature-sensitive element is provided, and said signal processing unit measures a temperature of substance in the vicinity of said pressure sensor by using an output signal transmitted from said temperature-sensitive element.

3. An integrated sensor according to claim 1, wherein at least a strain-sensitive gauge element is provided at a surface of said diaphragm in said pressure sensor, and another surface of said diaphragm is connected to said first substrate.

4. An integrated sensor according to claim 1, wherein at least a strain-sensitive gauge element is provided at a surface of said diaphragm in said pressure sensor, said surface of said diaphragm at which said strain-sensitive gauge element is connected to said first substrate.

5. An integrated sensor according to claim 1, wherein a first electrode plate is provided at a position facing to said diaphragm, of said first substrate, said diaphragm being a conductive electrode, and a second electrode plate is provided at a position opposite to said first electrode plate so that said first and second electrode plate sandwiches said diagram, and said signal processing unit measures said pressure of said substance, based on a difference between, an electrostatic capacity between said first electrode plate and said diaphragm and an electrostatic capacity between said second electrode plate and said diaphragm.

6. An integrated sensor according to claim 1, wherein said pressure sensor is made of single crystal silicon, said first substrate is made of boro-silicated glass, and said pressure sensor is airtightly connected to said first substrate by a anodic bonding method.

7. An integrated sensor according to claim 1, wherein said pressure sensor is made of single crystal silicon, and an oxidation film is formed at a surface area exposed to said substance, of said pressure sensor.

8. An integrated sensor according to claim 1, wherein said pressure sensor is made of single crystal silicon, and a nitriding film is formed at a surface area exposed to said substance, of said pressure sensor.

9. An integrated sensor according to claim 1, wherein said pressure sensor is made of single crystal silicon, and a corrosion-resistant metal film is formed at a surface area exposed to said substance, of said pressure sensor.

10. An integrated sensor according to claim 1, wherein each of said first conductive film and said second conductive film is made of a corrosion-resistant metal film.

11. An integrated sensor according to claim 1, wherein, for at least one of said first substrate and said second substrate, a through-hole is provided for electrically connecting a conductive film on a surface of said substrate and a conductive film on another surface of said substrate.

12. An integrated sensor according to claim 1, wherein said first conductive film and said second conductive film are connected to terminals provided at said signal processing unit via electrical connection wires, and a covering member for protecting said first conductive film, said second conductive film and said electrical connection wires from said substance, is attached to at least said second substrate.

13. An integrated sensor according to claim 1, wherein said pressure of said substance is led to a surface of said diaphragm via said first pressure admitting entrance and said second pressure admitting entrance, and another surface of said diaphragm is contained in an isolation chamber.

14. An integrated sensor according to claim 13, wherein a pressure of said isolation chamber is kept constant.

15. An integrated sensor according to claim 13, wherein said isolation chamber is kept as an almost vacuum state.

16. An integrated sensor according to claim 13, wherein at least one pressure leading path to said isolation chamber is provided to set said pressure of said isolation chamber as a desired level.

17. An integrated sensor according to claim 13, wherein said substance to be measured is liquid, a pressure of said liquid is led to said a surface of said diaphragm, and a pressure leading path to said isolation chamber is provided to set said pressure of said isolation chamber as an atmosphere pressure.

18. An integrated sensor according to claim 13, wherein said substance is fluid flowing in a pipe in which an orifice is provided, a pressure of said fluid in the upstream of said orifice is led to a surface of said diaphragm via said first pressure admitting entrance and said second pressure admitting entrance, and a pressure leading path is connected to said isolation chamber, in order to lead a pressure of said fluid in the downstream of said orifice to another surface of said diaphragm.

19. An integrated sensor according to claim 17, wherein at least a part of the signal processing unit is placed over a surface of liquid, which is separated from and connected to said pressure sensor with a water-proofing wire.

20. An integrated sensor according to claim 17, wherein at least a part of the signal processing unit is placed over a surface of liquid, which is separated from and electrically connected to said pressure sensor, a pressure leading path is connected between said signal processing unit and said isolation chamber, and at least a signal transmitting wire for connecting said signal processing unit and said pressure sensor is provided in said pressure leading path.

21. A fluid management system including a fluid storing part, a fluid feeding part with a first control valve, for flowing said fluid into said fluid storing part, a fluid draining part with a second control valve, for draining said fluid from said fluid storing part, a control part for adjusting a level of said fluid in said fluid storing part by controlling said first control valve at said fluid feeding part and said second control valve at said fluid draining part, wherein said integrated sensor according to claim 17 is arranged in said fluid storing part, and said control part for adjusting said level of fluid in said fluid storing part by controlling said first control valve, detects the specific conductance of said fluid expressing a quality of said fluid, and generates an alarm if the detected specific conductance is out of a predetermined range, based on output signals transmitted from said integrated sensor.

* * * * *